US006777235B1

(12) United States Patent
Ong et al.

(10) Patent No.: US 6,777,235 B1
(45) Date of Patent: Aug. 17, 2004

(54) COMPLEMENTATION TRAP

(75) Inventors: Christopher J. Ong, Vancouver (CA); John J. Priatel, West Vancouver (CA); Frank R. Jirik, Vancouver (CA)

(73) Assignee: The University of British Columbia (CA)

(*) Notice: Subject to any disclaimer, the term of this patent is extended or adjusted under 35 U.S.C. 154(b) by 0 days.

(21) Appl. No.: 09/295,464

(22) Filed: Apr. 19, 1999

Related U.S. Application Data (63) Continuation of application No. PCT/CA98/00677, filed on Jul. 10, 1998.

(30) Foreign Application Priority Data

Jul. 11, 1997 (CA) .............................................. 2205888

(51) Int. Cl.[7] .......................... C12N 15/87; C12Q 1/68; A01K 67/027
(52) U.S. Cl. ............................ 435/455; 435/6; 435/325; 435/320.1; 435/465; 435/462; 435/463; 536/23.2; 536/23.5; 536/23.7; 800/18
(58) Field of Search .......................... 435/6, 325, 320.1, 435/455, 462, 463, 465; 536/23.2, 23.5, 2.7; 800/18

(56) References Cited

U.S. PATENT DOCUMENTS

| 5,362,625 | A | 11/1994 | Krevolin |
| 5,364,783 | A | 11/1994 | Ruley |
| 5,523,226 | A | 6/1996 | Wheeler |
| 5,525,490 | A | 6/1996 | Erickson et al. |
| 5,652,128 | A | 7/1997 | Jarvik |
| 6,207,371 | B1 * | 3/2001 | Zambrowicz et al. .......... 435/6 |
| 6,303,327 | B1 | 10/2001 | Von Melchner |

FOREIGN PATENT DOCUMENTS

| CA | 2166850 | 7/1996 |
| CA | 2217545 | 10/1996 |
| CA | 2246414 | 8/1997 |
| CA | 2205888 | 1/1999 |
| EP | 0 514 173 | 11/1992 |
| WO | WO 98/24918 | 6/1998 |

OTHER PUBLICATIONS

Merriam–Webster's Collegiate Dictionary, pp. 766, 1997.*
Chen et al Proc. Nat. Acad. Sci. USA 88: 11368–11372, See abstract; p. 11368, column 1, last sentence of second paragraph; and p. 11369, column 2, lines 8–11 of first full paragraph, Dec. 1991.*
Andres et al J. Biol. Chem. 268(2): 1383–1390, see abstract, Jan. 1993.*
Moosmann et al Nucl. Acids Res. 24(6): 1171–1172, See entire document, Mar. 1996.*
Severne et al EMBO J. 7(8): 2503–2508, See p. 2504, column 1, lines 20 and 21 of Fig. 1 legend, Aug. 1988.*
Baskar et al J. Virology 70(5): 3207–3214, See entire document, especially abstract, May 1996.*
Choi et al. Mol. Cell. Biol. 11(6): 3070–3074, See entire document, especially abstract, Dec. 1991.*
Jang et al (Enzyme 44(1–4): 292–309, abstract only, 1990.*
Alouani S. et al, Eur J Cell Biol. (1993) 62(2):324–32.
Araki et al. Nucleic Acids Res. (1997) 25(4):868–872.
Brini M. et al. J Biol Chem. (1995) 270(17):9896–903.
Boggs S.S. et al. Exp Hematol. (1986) 14(10):988–94.
Breindl M. et al. Cell. (1984) 38(1):9–16.
Brenner DG. et al. Proc Natl Acad Sci U S A. (1989) 86(14):5517–21.
Chowdhury K. et al. Nucleic Acids Res. (1997) 25(8):1531–1536.
Dang C.V. et al. Mol Cell Biol. (1991) 11(2):954–62.
Doetschman T.C. et al. J Embryol Exp Morphol. (1985) 87:27–45.
Dziennis S. et al. Blood. (1995) 85(2):319–329.
Forrester L.M. et al. Proc Natl Acad Sci U S A. (1996)93(4):1677–1682.
Friedrich G. & Soriano P. Genes Dev. (1991) 5(9):1513–23.
Friedrich G. & Soriano P. Methods Enzymol. (1993) 225:681–701.
Goebl M.G. and Petes T.D. Cell (1986) 46(7):983–92.
Gogos JA, et al: J Cell Biol: (1996) 134(4):834–47.
Gossler A. et al. Science (1989) 244(4903):463–465.
Hill D.P. and Wurst W. Methods Enzymol. (1993) 225:664–681.
Imai Y. et al. Brain Res Mol Brain Res. (1995)31(1–2):1–9.
Jahner D. and Jaenisch R. Nature (1985) 315(6020):594–597.
Kerr W.G. et al. Cold Spring Harb Symp Quant Biol. (1989) 54 Pt 2:767–76.
Kratochwil K. et al. Cell (1989) 57(5):807–16.
Lakso M. et al. Proc Natl Acad Sci U S A. (1992) 89:6232–6236.
Lieschke G.J. and Dunn A.R. Exp Hematol. (1995)23(4):328–334.

(List continued on next page.)

*Primary Examiner*—Dave T. Nguyen
*Assistant Examiner*—Richard Schnizer
(74) *Attorney, Agent, or Firm*—Townsend & Townsend & Crew LLP (57) ABSTRACT

Methods and DNA constructs are provided for detection and manipulation of a target eukaryotic gene whose expression is restricted to certain tissues or specialized cell types. The methods include transforming a cell with a first indicator component under the control of a promoter selected for its restricted expression in a particular cell or tissue. The cell is also transformed with a gene trap vector encoding a second indicator component. The cell is allowed to differentiate to produce specialized cell or tissue which is monitored for expression of both the first and second indicator components, thereby detecting a gene into which the trap vector has integrated which is expressed in the same cell or tissue type as the selected promoter.

13 Claims, 1 Drawing Sheet

OTHER PUBLICATIONS

MacLeod D. et al. Nucleic Acids Res. (1991) 19(1):17–23.
Mohler W.A. and Blau H.M. Proc. Natl Acad Sci U S A. (1996) 93(22):12423–12427.
Mountford P. et al. Proc Natl Acad Sci U S A. (1994) 91(10):4303–7.
Nagy A. et al. Proc Natl Acad Sci U S A. (1993) 90(18):8424–8428.
Niwa H et al. J Biochem (Tokyo). (1993) 113(3):343–9.
Reddy S. et al. J Virol. (1991) 65(3):1507–1515.
Rickhert R.C. et al. Nucleic Acids Res. (1997) 25(6):1317–1318.
Risau W. et al. Development (1988) 102(3):471–8.
Rohdewohld H. et al. J Virol. (1987) 61(2):336–43.
Scherdin U. et al. J Virol. (1990) 64(2):907–912.
Shirai M. et al. Zoolog Sci. (1996) 13(2):277–283.
Skarnes W.C. et al. Genes Dev. (1992) 6(6):903–918.
Skarnes W.C. Curr Opin Biotechnol. (1993) 4(6):684–689.
Soininen R. et al. Mech Dev. (1992) 39(1–2):111–123.
Townley D.J. et al. Genome Res. (1997) 7(3):293–8.
Vijaya S. et al. J Virol. (1986) 60(2):683–92.
Von Melchener H. et al. Proc Natl Acad Sci U S A. (1990) 87(10):3733–3737.
Von Melchener H. et al. Genes Dev. (1992) 6(6):919–927.
Wiles M.V. and Keller G. Development (1991) 111(2):259–267.
Wilson C. et al. Genes Dev. (1989) 3(9):1301–13.
Wood S.A. et al. Nature (1993) 365(6441):87–89.
Wurst W. et al. Genetics (1995) 139(2):889–899.
Irmgard St. et al. Molecular and Cellular Biology (1998) 18(5):30181–3088.
International Search Report PCT/CA 98/00677, Jan. 21, 1999.
Fields, et al., "A novel genetic system to detect protein–protein interactions," *Nature*, 340:245–246 (1989).
Luo, et al., "Mammalian Two–Hybrid System: A Complementary Approach to the Yeast Two–Hybrid System," *Biotechniques*, 22(2):350–352 (1997).

* cited by examiner

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:PCR
      amplification oligo 1 polylinker sequence 5' of
      beta-gal from beta-galactosidase plasmid

<400> SEQUENCE: 1
aactgcagta cccgcggccg c                                           21

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence:PCR
      amplification oligo 2 introduces stop codons
      corresponding to amino acid 85 of E. coli lacZ
      from beta-galactosidase plasmid

<400> SEQUENCE: 2
```

```
                                     -continued aactgcagtt attactcagg aagatcgcac tccagc                                36

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence:Oligo 1
      deletes first 41 amino acids from E. coli
      beta-galactosidase N-terminal sequence

<400> SEQUENCE: 3
cgggatccca agatctgggc ccgcaccgat cgcccttcc                              39

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:Oligo 2
      deletes first 41 amino acids from E. coli
      beta-galactosidase N-terminal sequence

<400> SEQUENCE: 4
cgggatccat cgataatttc accgccg                                          27

<210> SEQ ID NO 5
<211> LENGTH: 12
<212> TYPE: DNA
<213> ORGANISM: Artificial Sequence
<220> FEATURE:
<223> OTHER INFORMATION: Description of Artificial
      Sequence:self-overlapping oligomer

<400> SEQUENCE: 5
catggagatc tc                                                          12
```

COMPLEMENTATION TRAP

This Application is a continuation under 37 CFR 1.53(b) of PCT/CA98/0067, filed 10 Jul. 1998.

FIELD OF THE INVENTION

The present invention relates to gene entrapment vectors and their use in gene discovery, and their use in screening for or making cells and organisms that are mutated for such genes. This invention also relates to the use of such entrapment vectors to identify tissue specific transcription control elements such as promoters and enhancers and for generating transgenic animals displaying restricted expression of transgenes. This invention also relates to trap vectors comprising a splice acceptor and a sequence encoding a reporter gene.

BACKGROUND OF THE INVENTION

Genomic based drug discovery is largely dependent upon the identification of specific genomic targets. Thus, cloning, sequencing, and identification of function of mammalian genes is a first priority in a genomic based drug discovery. In particular, it is important to identify and make use of genes which are spacially and/or temporally regulated in the organism.

Animal model systems such as the fruit fly and the worm are often used in gene identification because of ease of manipulation of the genome and ability screen for mutants. While these systems have their limitations, large numbers of developmental mutations have been identified in those organisms either by monitoring the phenotypic effects of mutations or by screening for expression of reporter genes incorporated into developmentally regulated genes.

Many features of the mouse make it the best animal model system to study gene function. However, the mouse has not been used for large scale classical genetic mutational analysis because random mutational screening and analysis is very cumbersome and expensive due to long generation times and maintenance costs.

A disadvantage in using animal models for the identification of genes is the need to establish a transgenic animal line for each mutational event. This disadvantage is alleviated in part by using embryonic stem (ES) cell lines because mutational events may be screened in vitro prior to generating an animal. ES cells are totipotent cells isolated from the inner cell mass of the blastocyst. Methods are well known for obtaining ES cells, incorporating genetic material into ES cells, and promotion of differentiation of ES cells. ES cells may be caused to differentiate in vitro or the cells may be incorporated into a developing blastocyst in which the ES cells will contribute to all differentiated tissues of the resulting animal. Vectors for transforming ES cells and suitable genes for use as reporters and selectors are also well known.

Gene entrapment strategies have been employed to identify developmentally regulated genes. One type of entrapment vector is called a "promoter trap", which consists of a reporter gene sequence lacking a promoter. Its integration is detected when the reporter is integrated "in-frame" into an exon. "Gene trap vectors" target the much more prevalent introns of the eucaryotic genome. The latter vectors consist of a splice-acceptor site upstream from a reporter gene. Integration of the reporter into an intron results in a fusion transcript containing RNA from the endogenous gene and from the reporter gene sequence.

Gene trap vectors may be made more efficient by incorporation of an internal ribosomal entry site (IRES) such as that derived from the 5' non-translated region of encephalomyocarditis virus (EMCV). Placement of a IRES site between the splice acceptor and the reporter gene of a gene trap vector means that reporter gene product need not be translated as a fusion product with the endogenous gene product, thereby increasing the likelihood that integration of the vector will result in expression of the reporter gene product.

Examples from the literature of the use of promoter and gene trap vectors as well as such vectors including an IRES sequence, are listed below. Some examples involve the identification of developmentally regulated or tissue specific events making use of ES cell lines.

1. Canadian Patent application no. 2,166,850 (open for public inspection Jul. 11, 1996) *Vectors and the Use Thereof for Capturing Target Genes*: describes the use of transmembrane sequence encoding gene trap vectors to isolate and identify secretory proteins. Also see U.S. Pat. No. 5,767,336 issued Jun. 16, 1998.
2. U.S. Pat. No. 5,364,783 issued Nov. 15, 1994. *Retrovirus Promoter Trap Vectors*: describes retroviral vectors that are used to isolate transcriptionally active chromosomal regions and to identify promoter sequences. The reporter gene is placed in the U3 or U5 control region of the retrovirus.
2. Gossler, A., et al. (1989). *Mouse Embryonic Stem Cells and Reporter Constructs to Detect Developmentally Regulated Genes*. Science 244:463–465: describes the use of enhancer trap gene trap vectors for use in identifying developmentally regulated genes. The gene trap vector consists of the mouse En-2 splice acceptor upstream from lacZ (reporter) and a selector gene (hBa-neo).
3. Von Melchner, H., et al. *Isolation of Cellular Promoters by Using a Retrovirus Promoter Trap*. Proc. Natl. Acad. Sci. USA 1990, 87:3733–3737.
3. MacLeod, D., et al.: *A Promoter Trap in Embryonic Stem (ES Cells Selects for Integration of DNA into CpG Islands*. Nucleic Acids Res. 1991, 19:17–23.
4. Reddy, S., et al.: *Retrovirus Promoter-Trap Vector to Induce lacA Gene Fusions in Mammalian Cells*. J. Virol. 1991, 65:1507–1515.
5. Brenner, D. G., et al.: *Analysis of Mammalian Cell Genetic Regulation in Situ by Using Retrovirus-Derived Portable Exons Carrying the Escherichia coli lacZ Gene*. Proc. Natl. Acad. Sci. USA. 1989, 86:5517–5521.
6. Kerr, W. G., et al.: *Transcriptional Defective Retroviruses Containing lacZ for the in Situ Detection of Endogenous Genes and Developmentally Regulated Chromatin*. Cold. Spring. Harb. Symp. Quant. Biol. 1989, 54:767–776.
7. Friedrich, G. and Soriano, P.: *Promoter Traps in Embryonic Stem Cells: A Genetic Screen to Identify and Mutate Developmental Genes in Mice*. Genes. Dev. 1991, 5:1513–1523.
8. Skarnes, W. C., et al.: *A Gene Trap Approach in Mouse Embryonic Stem Cells: The lacZ Reporter is Activated by Splicing, Reflects Endogenous Gene Expression, and is Mutagenic in Mice*. Genes Dev, 1992, 6:903–918: describes gene trapping that results in activation of lacZ by splicing to endogenous exons and production of a fusion protein whose expression pattern mimics that of the endogenous gene. The resulting integration and fusion is mutagenic. Using 5' RACE, the endogenous gene activated with three lacZ-based gene-trap insertions was cloned and the effectiveness of the En-2 splice acceptor site was demonstrated. For two insertions, the pattern of lacZ expression in embryos was shown to match the normal distribution of endogenous transcripts. Two of the three insertions tested cause phenotypic abnormalities in mice. One of those was an insertion into a novel gene expressed widely during development that causes perinatal death in homozygous animals. The other is an insertion into a zinc-finger gene expressed in neural cells that results in mild growth retardation after birth.

9. Von Melchner, H., et al.: *Selective Disruption of Genes Expressed in Totipotent Embryonal Stem Cells*. Genes. Dev. 1992, 6:919–927: where sequences upstream of nine retroviral promoter-trap insertions were cloned using if inverse PCR. Flanking probes from five ES cell lines detected transcripts, and one clone is identified as the REX-I transcription factor. Two of four lines transmitted to the germline caused embryonic-lethal phenotypes.

10. Sheriden, U., et al.: *Transcriptionally Active Genomic Regions are Preferred Targets for Retroviral Integration*. Mol. Cell. Biol. 1990, 64:907–912.

11. Vijaya, S., et al.: *Acceptor Sites for Retroviral Integrations Map Near DNase 1-Hypersensitive Sites in chromatin*. J. Virol. 1986, 60:683–692.

12. Rohdewold, H., et al.: *Retrovirus Integration and Chromatin Structure: Moloney Murine Leukemia Proviral Integration Sites Map near DNAse I Hypersensitive Sites*. J. Virol 1987, 61:336–343.

13. Boggs, S. S., et al.: *Efficient Transformation and Frequent Single Site, Single Copy Transcription of DNA can be Obtained in Mouse Erytholeukemia Cells Transformed by Electroporation*. Exp Rematol 1986, 149:988–994.

14. Soininen, R., et al.: *The Mouse Enhancer Trap Locus I (Etl-1): A Novel Mammalian Gene Related to Drosophila and Yeast Transcriptional Regulator Genes*. Mech Dev 1993, 39:111–123.

15. Niwa, H., et al.: *An Efficient Gene-Trap Method using Poly A Trap Vectors and Characterization of Gene-Trap Events*. J. Biochem 1993, 113:343–349.

16. Breindl, J. K., et al.: *Retrovirus-Induced Lethal Mutation in Collagen I Gene of Mice is Associated with Altered Chromatin Structure*. Cell 1984, 38:9–16.

17. Jahner, D. and Jaenisch, R.: *Retrovirus-Induced de Novo Methylation of Flanking Host Sequences Correlates with Gene Inactivity*. Nature 1985, 315:594–597.

18. Kratochwil, K.: *Retroviral-Induced Mutation in Mov 13 Mice Affects Collages I Expression in a Tissue-Specific Manner*. Cell 1989, 57:807,816.

19. Goebl, M. G. and Petes, T. D.: *Most of the Yeast Sequences are Not Essential for Cell Growth and Division*. Cell 1986, 46:983–922.

20. Wilson, C., et al.: *P-element Mediated Enhancer Detection: An Efficient Method for Isolating and Characterizing Developmentally Regulated Genes in Drosophila*. Genes. Dev. 1989, 3:1301–1313.

21. Wood, S. A., et al.: *Non-Injection methods for the Production of Embryonic Stem Cell-Embryo Chimeras*. Nature 1993, 365:87–89: describes time-saving methods for generating ES cell derived chimeras by morulae aggregation. These can be used to more easily carry out a prescreen based on embryonic expression of the reporter.

22. Doetschman,. T. C.: *The in Vitro Development of Blastocyst-Derived Embryonic Stem Cell lines: Formation of Visceral Yolk Sac, Blood Islands and Myocardium*. J. Embryo. Exp. Morph. 1985, 97:27–45.

23. Risau, W., et al.: *Vasculoaenesis and Angiogenesis in Embryonic-Stem-Cell Derived Embryoid Bodies*. Development 1988, 102:471–478.

24. Wiles, M. V. and Keller, G.: *Multiple Hematopoetic Lineages Develop from Embryonic Stem (ES) Cells in Culture*. Development 1991, 111:259–267.

25. Rossant, J., et al.: *A large Scale Gene Trap Screen for Insertional Mutations in Developmentally Regulated Genes in Mice*. Genetics 1995, 139:889–899: describes the use of a gene trap vector to mutagenize ES cells and the screening of ES clones by injection into blastocysts and assaying for reporter gene expression in 8,5 dpc chimeric mouse embryos.

26. Thompson, et al.: *Gene Trapping in Differentiating Cell Lines: Regulation of the Lysosomal Protease Cathepsin B in Skeletal Myoblast Growth and Fusion*: describes the use of a retroviral promoter trap vector in the myoblast cell line C2C12, to identify and isolate skeletal muscle specific genes.

27. Shiria, et al.: *A Gene Trap Strategy to Identify Genes That Are Expressed in the Developing Mouse Nervous System*. Zoological Science 1996, 13:277–283: describes use of a gene trap vector called pSneoNlacZA in ES cells. ES clones were allowed to differentiate in vitro in a suspension culture system into neurons, neuro-glia precursors cells. Neuronal cells were identified by using antibodies reactive against neuron specific proteins. Three clones that were immunohistochemically positive and $\beta$-gal positive were identified.

28. Imai, et al.: *Cloninc of Retinoic Acid Induced Gene, GT1, in Embryonal Carcinoma Cell Line P19: Neuron Specific Expression in Mouse Brain*. Molecular Brain Research. 1995, 31:1–9: describes the use of a gene trap vector in mouse P19 embryonal carcinoma cell line which can be reproducibly differentiated to neurons and glial cells upon treatment with retinoic acid. Assay for up or down regulation of $\beta$-gal activity and immunohistochemistry showed localization in neurons.

29. Forrester, et al.: *An Induction Gene Trap Screen in Embryonic Stem Cells: Identification of Genes that Respond to Retinoic Acid in vitro*. Proc. Nat. Acad. Sci. USA 1996, 93:1677–82: where a gene trap vector was used in ES cells and treated with retinoic acid, with a screen for genes that are induced or repressed upon retinoic acid exposure.

30. Hill, D. P. and Wurst, W. (1993): *Screening for Novel Pattern Formation Genes Using Gene Trap Approaches*, Methods in Enzymology 225:664–681.

31. Kim, D. G., et al. (1992): *Construction of a Bifunctional mRNA in the Mouse by Using the Internal Ribosomal Entry Site of the Encephalomyocarditis Virus*. Molecular and Cellular Biology, 12: 3636–3634: describes construction of vectors comprising a promoter driven selector (eg. neo) followed by EMCV 5' non-translated region and either lacZ or cat, and transfection of murine ES cells with the vectors. The IRES of the EMCV permitted more efficient translation of the reporter in resulting chimeric embryos which also expressed the selection gene.

32. Chowdhury, K. et al. (1997): *Evidence for the Stochastic Integration of Gene Trap Vectors into the Mouse Germline*. Nucleic Acids Research, 25: 1531–1536: describes construction of a gene trap vector comprising an EN-2 splice acceptor followed by an IRES sequence and B geo (lacZ reporter fused with neo selector). Murine ES cells were transfected and neomycin resistant colonies were monitored for $\beta$-galactosidase activity indicative of lacZ expression Molecular cloning of trapped exons was carried out using 5'-RACE.

33. D. P. Hill and W. Wurst (1993): *Screening for Novel Pattern Formation Genes Using Gene Trap Approaches*; Methods in Enzymology 225: 664–681.

34. G. Friedrich and P. Soriano (1993): *Insertional Mutagenisis by Retroviruses and Promoter Traps in Embryonic Stem Cells*; Methods in Enzymology 225: 681–701.

35. W. C. Skarnes (1993): *The Identification of New Genes: Gene Trapping in Transgenic Mice*; Current Opinion in Biotechnology 4: 684–689.

Regardless of the model, the process of identifying and manipulating tissue specific genes requires elaborate screening procedures to link a mutation to a particular spacial/temporal scheme or event whereby the mutation is detected in the relevant tissue. It is therefore desirable to make screening and manipulation of new spacial/temporally regulated genes in all eucaryotic models more efficient.

SUMMARY OF INVENTION

This invention makes use of known genes whose expression is restricted to specific tissue, tissues or specialized cells ("restricted expression") to facilitate identification and manipulation of new genes and their associated transcription control elements which have similar patterns of expression.

Accordingly, this invention provides a method of detecting a target gene having restricted expression in a eucaryotic organism, which comprises the steps of:

(i) transforming a eucaryotic cell with a DNA sequence encoding a first indicator component under the control of a promoter having restricted expression;

(ii) transforming the cell of (i) or a descendent of the cell of step (i), by operably integrating into the cell's genome DNA lacking a promoter but which comprises a sequence encoding a second indicator component;

(iii) producing tissue or specialized cells from the cell of (ii); and (iv) monitoring the tissue or specialized cells of (iii) for a detectable indicator resulting from both the first and second indicator components.

This invention also provides a method of obtaining a gene, a part of a gene, transcription control element or other nucleotide sequence, having restricted expression which includes isolating endogenous DNA flanking of the sequence encoding the second indicator component from a cell or descendent of a cell prepared as described above in which the detectable indicator is found. This invention also provides a method of modifying the gene, transcriptional control element or other nucleotide sequence obtained as described above which includes modification of the endogenous DNA which flanks the coding sequence of the second indicator component.

This invention also provides a method of providing a eucaryotic organism producing a detectable indicator in a specialized cell or tissue of the organism which includes growing a multi-cellular eucaryotic organism from a cell or cell descendent from a cell prepared as described above, in which the detectable indicator is found. The organism may also express in the specialized cell or tissue, the product of heterologous DNA expressed with DNA flanking of the second indicator component of the detectable indicator.

This invention makes use of a gene entrapment strategy whereby a detectable indictor is detected when more than one component of the indicator is expressed in the same cell. One method of this invention involves stable and operable insertion of a nucleic acid construct which includes one indicator component of the complementation trap under the control of a known promoter having restricted expression into the genome of the cell. This is followed by further transformation of the cell, or a cell derived from the previously transformed cell, by insertion into the cell's genome of a trap vector which includes a DNA which encodes a second indicator component. Insertion of the trap vector into an endogenous gene may result in the transcription of both the endogenous gene and the second indicator component under control of the endogenous promoter and subsequent translation of the second component. If the trap vector integrates into an endogenous gene which is expressed in the same cell or tissue type as the first indicator component, a indicator resulting from the combination of the first and second indicator components may be detected. Thus, this invention allows one to distinguish target eukaryotic genes which are expressed in the same cell or tissue type as the promoter controlling the first component of the entrapment system. This system, as embodied by this invention is termed a "complementation trap".

This invention provides a DNA construct comprising a splice acceptor upstream of a sequence encoding a component of a detectable indicator according to this invention. The component may be, for example, an enzyme fragment or subunit, or an enzyme functional in a pathway leading to production of a detectable indicator. This invention also provides a DNA construct comprising a promoter having restricted expression upstream of a sequence encoding a component of a detectable indicator as described above.

This invention also provides a first DNA construct comprising a splice acceptor upstream of a sequence encoding a first peptide selected from the group consisting of an alpha peptide and an omega peptide of β-galactosidase (β-gal), wherein the first peptide lacks β-gal activity but is capable of alpha complementation to produce active β-gal. This invention also provides a eucaryotic cell and a non-human, multi-cellular eucaryotic organism having operably and stably incorporated into its genome, the first DNA construct described above. This invention also provides a kit including the first DNA construct and, a second DNA construct comprising a promoter having restricted expression upstream of a sequence encoding a second β-gal peptide selected such that the second peptide is capable of alpha complementation with the first peptide. This invention also provides a eucaryotic cell and a non-human, multi-cellular eucaryotic organism having operably and stably incorporated into its genome the first DNA construct and which also expresses the second DNA construct.

Trap vectors useful for this invention, including the above-described first DNA construct, may also contain additional elements such as an internal ribosome entry sequence (IRES) upstream of the second indicator component (eg. the first peptide) or, sequences that allow for directional integration of a heterologous gene, such as a recognition site for site specific recombination (eg. lox)

This invention may be used to identify tissue or cell type specific genes. For example, a nucleic acid construct containing the coding sequence of a first indicator component under control of a known tissue specific promoter is "seeded" into cells which may be made to differentiate or whose nuclear material may be incorporated into cells which are capable of differentiation. The second component is then introduced into a cell having the "seeded" construct, by means of the trap vector. The resulting cells, or cells derived from those cells (eg. progeny), are then induced to differentiate (for example by addition or withdrawal of a chemical inducer/repressor) or allowed to spontaneously differentiate. The cells are then screened for activity of the indicator which will occur in the cell or tissue type in which the promoter is functional.

This invention is particularly useful for screening cell or tissue specific genes or transcriptional control elements such as promoters and enhancers, in any animal from which embryonic stem (ES) cell lines may be obtained. The ES cell is subjected to the complementation trap process described above. The ES cells are then allowed to differentiate in vitro and cells are screened for the indicator. ES cells demonstrating expression of the indicator may be introduced into a blastocyst to produce an animal which will exhibit the same pattern of expression. Where introduction of the trap vector results in disruption of the target gene, the animal resulting from the mutated ES cells will be useful as a "knock-out" animal useful for study of the target gene. Alternatively, location of the trap vector into the endogenous gene will provide means for subsequent disruption of the target gene for production of "knock-out" animals. The trap vector of this invention may be used as a means for locating, cloning, sequencing, and further mutation of the target gene or promoter or enhancer sequences associated with the target gene.

This invention will make new transcriptional control elements available for use in making new transgenic animals displaying cell, tissue or organelle specific expression of transgenes. Promoters made available by use of this invention may themselves be made to control the first indicator component in the complementation trap of this invention in a "leap-frog" procedure whereby new genes having the same restriction pattern as the promoter or may be located.

DESCRIPTION OF SPECIFIC EMBODIMENTS

The term "eucaryotic organism" in this specification means any multi-cellular eucaryote having cells which are differentiated to specific cell or tissue types and includes plant or animal organisms, including, but not restricted to: Drosophila, nematodes, fish and mammals. The method of this invention may be carried out to transform any eucaryotic cell which is capable of differentiation into tissue or specialized cell types and includes any bi- or multipotent eucaryotic cell as well as a differentiated eucaryotic cell whose nuclear material may be transplanted to a bi- or multipotent cell. An example of the latter situation is where differentiated cells are transformed according to the method of this invention and whose nuclear material is subsequently placed in a enucleated ovum or similar vehicle which is then caused to become bi- or multipotent and thus capable of differentiation. Particularly suitable for this invention are totipotent cells such as ES cells.

The term "restricted expression" in this specification means the restriction of a transcription control element (such as a promoter or an enhancer) or the restriction of expression of a gene, such that the aforesaid function or expression occurs in a particular tissue or cell type in a eucaryotic organism. Thus a gene or transcription control element having "restricted expression" is a tissue or cell specific gene or control element.

The "detectable indicator" of this invention is a detectable event which results from the expression of more than one indicator component in a cell.

This invention may be used to isolate, characterize, and modify genes that are differentially expressed. Tissue or cell specific genes may be located by using any tissue or cell specific promoter to drive the first indicator component of the complementation trap system. An example of this invention used to identify genes that are expressed in myeloid cells of the hemopoietic system, would be to make use a known myeloid cell/tissue specific promoter such as CD11b to drive the expression of the first indicator component of the complementation trap system. Examples of other tissue restricted promoters are listed below but this invention may be carried out using any promoter with restricted expression:

Neural: Neuron specific RIβ sub unit of cAMP-PK promoter, Tryptophan Hydroxylase promoter, Neural specific enolase promoter, Tyrosine hydroxylase promoter, Tαl α-tubulin promoter;

Lung: α1 collagen gene promoter, rat clara cell 10 protein PROMOTER, human surfactant protein SP-C promoter, preproendothelin promoter;

Liver: human apolipoprotein E promoter;

Heart: alpha B crystallin promoter, murine alpha myosin heavy chain promoter;

Thymus: lck proximal promoter;

T cells: CD2 promoter, CD4 promoter, CD3 promoter;

B cells: IGEμ, CD19 promoter;

Osteoclast—and osteoblast specific promoter: Mouse pro-α1(I) promoter, Tartrate Resistant Acid Phosphatase (TRAP) promoter, CD11b promoter.

One example of a detectable indicator that may be used in this invention occurs as the result of the well-known phenomenon of alpha complementation of β-galactosidase (β-gal) fragments. The β-gal enzyme can be divided into two peptides called alpha and omega. β-gal enzyme activity is present only when both alpha and omega peptides are present in the same cell. The alpha and the omega peptide alone show no detectable enzymatic activity. β-galactosidase enzyme activity can be detected by using commercially available enzyme substrates such as X-gal™ which turns blue upon hydrolysis by β-galactosidase. Other substrates such as Galacton-plus™ (Clontech) produce light upon enzymatic cleavage allowing for detection using a luminometer while other substrates produce fluorescent products detectable by flow cytometry or fluorescence microscopy. The Galacto-star™ kit (Tropix, Inc.; Bedford, Mass., U.S.A.) which provides a chemiluminescent assay is particularly useful for preferential detection of β-gal over endogenous mammalian β-gal activity.

Alpha complementation of β-gal may be accomplished in eucaryotic cells, including yeast and mammalian cells; see: Mohler, W. A. and Blau, H. M. 1996. *Gene Expression and Cell Fusion Analyzed by lacZ Complementation in Mammalian Cells*. Proc. Natl. Acad. Sci. 93:12423–12427; and Moosman, P. and Rusconi, S. (1996). *Alpha Complementation of lacZ in Mammalian Cells*. Nucleic Acids Res. 24:1171–1172.

In order to identify genes that are expressed in myeloid cells, one may use the CD11b promoter to drive expression in myeloid cells of a sequence encoding one of the β-gal peptides (eg. the alpha fragment comprising about 85 or more N-terminal amino acids of β-gal). The trap vector would include a splice acceptor sequence, a sequence encoding an omega fragment of β-gal (eg. inactive β-gal peptide lacking a N-terminal portion of β-gal), and optionally, an IRES sequence and a lox site for directed integration of heterologous genes. The trap vector may optionally contain a second reporter system to identify and characterize the endogenous gene expression pattern. The trap vector may also contain a selectable marker cassette. Another approach would be to introduce the first indicator component to be under control of an endogenous promoter having restricted expression endogenous gene via homologous recombination. For example, in order to obtain expression in early immature B lymphocytes, a sequence encoding the first indicator component may be introduced by homologous recombination into the CD 19 gene in a mouse ES cell germline such that the expression of the indicator component is under the control of the CD 19 gene (eg. see: Rickert, R. C. et al. (1997): *B Lymohocyte-specific, Cre-mediated Mutagenisis in Mice*; Nucleic Acids Research, 25:1317–1318).

Stable lines of ES cells bearing the tissue restricted promoter driving the alpha component are generated and tested for appropriate tissue restricted expression. Mutations are then introduced in the mouse genome by random integration of the omega peptide trap vector. Since the trap vector has a splice acceptor sequence fused to the omega component, integration of the trap vector into a gene intron results in splicing omega mRNA into the transcript of the endogenous gene and ultimately, expression of a fusion protein comprising of a portion of the endogenous protein and the omega subunit. Where a IRES is placed upstream of the omega component, the omega peptide is translated without being fused to the endogenous protein.

Individual integration/mutational events are propagated and replica plated. One fraction of the cells are allowed to undergo in vitro differentiation and are assayed for the indicator. If both β-gal subunits are expressed in the same cell, the indicator is detected whereas the components expressed individually in cells will not be detected. Thus, this procedure identifies integration/mutational events into genes that are expressed in the same given tissue cell type that is defined by the known tissue restricted promoter driving the first component.

Target genes into which the gene trap has integrated can be cloned and sequenced, for example, by 5' RACE PCR. Undifferentiated ES cells can be used to generate mice mutated for the respective gene. The endogenous tissue restricted promoter of the target gene can be characterised and heterologous genes can be inserted into the site by homologous recombination or site directed recombination, thus allowing the heterologous gene to be driven by the newly identified endogenous tissue restricted promoter.

A "leap-frog" procedure may be employed whereby the tissue specific promoter of the target gene may become the "known" promoter driving expression of the first indicator component. The example employing β-gal complementation described above may be accomplished regardless of which β-gal peptide is expressed in the target gene or under control of the known tissue specific promoter. Thus, cells when containing both β-gal peptide inserts have been shown to result in restricted expression of both peptides upon differentiation, a stored sample of the original transformed cells may be manipulated to remove or disrupt expression of the peptide whose expression is controlled by the "known" tissue restricted promoter. For example, the DNA which encodes the first indicator component under control of the known promoter may be flanked by lox sequences which permit the excision of the sequence encoding the first indicator from the genome with Cre recombinase. A trap vector may then be introduced comprising a splice acceptor and a coding sequence equivalent to that which has been removed or disrupted. Mutational events which result in expression of the new trap vector are detected because of the combination of the indicator component expressed as a result of the first introduced trap vector, plus the component expressed as a result of the second trap vector. Thus, genes having a pattern of expression similar to the first target gene may be located even if the pattern of expression differs from that of the original "known" promoter.

The foregoing description illustrates embodiments of this invention in which the first component is driven by a known promoter and the detectable indicator results from enzymatic complementation of proteins or peptides expressed from the first and second indicator component coding sequences. This invention may be carried out using any detectable gene products which exhibit intra-cistronic complementation. Other peptides which exhibit enzymatic complementation may be employed in this invention in the same manner as alpha and omega fragments of β-gal. Alternatively, the detectable indicator components may be subunits of a detectable protein which subunits are expressed from different genes or coding regions. An example would be the subunits of bacterial luciferase.

The following are further examples of different detectable indicators and components thereof which may be used in this invention:

(a) Transcriptional activation (two hybrid system): the detectable indicator results from transcription of a reporter gene which requires the presence of two genetic components; a DNA binding subunit and a transcriptional activating subunit. Both components need to be present in the same cell in order for expression of the reporter gene to occur and subsequent detection of the reporter gene product.

(b) Transcriptional activation (genetic recombination dependent): the detectable indicator results from transcription and expression of a reporter gene regulated by a tissue specific promoter which is conditional upon genetic recombination controlled by expression of a recombinase enzyme. For example, a stuffer DNA sequence (flanked by lox sequences) which prevents efficient transcription or expression of a reporter gene is removed by recombination that is mediated by a Cre recombinase enzyme allowing for expression of the reporter gene and subsequent detection of its product. Alternatively, a recombination event may be required to juxtapose the promoter/enhancer sequence with the reporter gene in the correct orientation to allow for the efficient expression of the reporter gene.

(c) Enzyme pathway: the detectable indicator is a product generated by the sequential action of two enzymes on a substrate. Alternatively, the detectable indicator may result from products produced by the action of two enzymes which interact in such a way as to generate a detectable signal. Alternatively, the detectable indicator results from activity of a first enzyme which is regulated by the activity of a second enzyme, (for example: enzymatic activity of first enzyme is dependant on a post translational modification mediated by a second enzyme, such as proteolytic activation, glycosylation or phosphorylation etc.).

(d) Selection/screening system: a selectable marker such as an antibiotic resistance gene is driven by a tissue specific promoter and a second reporter gene is used in a trap vector.

The cells are induced to differentiate and are subsequently placed under selection conditions that allow for the survival of only those cells expressing the selectable marker. Those cells are then screened for the expression of the second reporter.

(e) Co-expression of two reporter genes: one reporter is driven by a "known" tissue specific promoter and the second reporter is used in a trap vector. Differentiated cells are screened for expression of both reporter genes in the same cell.

Examples of suitable reporter genes that may be employed in the above-described examples are: β-galactosidase, alkaline phosphatase, blue fluorescent protein, green fluorescent protein (GFP), β-glucuronidase (GUS), Cre recombinase, Flp recombinase; luciferase, and their cell surface protein with antibodies that can detect its expression. Suitable selectable markers that may be used are: Neo-(neomycin phosphotransferase), Hygro-(hygromycin β-phosphotransferase), Puro—(puromycin n-acetyltransferase pac), HisD—(histidinol dehydrogenase), and Gpt—(xanthine/guanine phosphoribosyl transferase).

Examples of ES cell lines which may be used in this invention are: porcine (eg. U.S. Pat. No. 5,523,226 Transgenic Swine Compositions and Methods); murine (eg. D3, R1, CGR8, AB1ES cell lines); primate (eg. rhesus monkey); rodent; marmoset; avian (eg. chicken); bovine; rabbit; sheep; and horse.

A wide variety of cells may be targeted by the trap vectors of this invention, including stem cells, pluripotent cells such as zygotes, embryos, ES cells, other cells such as lymphoid and myeloid stem cells, neural stem cells, transformed cells such as tumour cells, infected cells differentiated cells, etc. The cells may be targeted in culture or in vivo. Vectors may be introduced into the cells by any convenient means. For example, with cells in culture, conventional techniques such as transfection (eg. lipofection, calcium phospace precipitation, electroporation, etc.), microinjection, viral infection etc. may be used. For cells within the organism, introduction may be mediated by virus, liposome, or any other convenient technique.

Examples of different trap vectors for use in this invention are as follows:

Gene trap: a promoterless reporter gene component carrying a splice acceptor sequence at the 5' end. Each vector will splice in the correct reading frame in 1 of 3 possible reading frames. The vector should integrate in to an intron sequence of a gene to result in a fusion transcript and a fusion protein product. The 5' sequence of the fusion transcript is encoded by the endogenous gene and the 3' sequence is encoded by the gene trap vector. Three gene trap vectors can be created for splicing into each of the three reading frames. The reporter gene lacks ATG translation start signal.

Gene trap (SA-IRES-reporter): a promoterless reporter gene containing a proper translation initiation sequence having a splice acceptor sequence (SA) followed by a IRES at the 5' end.

Exon trap: a reporter gene component lacking a splice acceptor and a mammalian initiator codon. Integration of this vector into an exon in the proper translational frame results in the production of a fusion protein.

Enhancer trap: reporter gene lacking a promoter but having a "minimal promoter" sequence encoding a TATA box and a transcriptional initiation site. These may be used to locate a target gene affected by an enhancer with restricted expression. The indicator must be monitored for enhanced expression in a particular cell type.

Promoter trap: promoterless reporter gene with appropriate translation initiation sequence. Insertion into an intron would not result in translation due to RNA processing. Integration immediately proximal to an endogenous promoter is required in order to have appropriate expression.

A splice acceptor (SA) includes the 3' end of an intron and the 5' end of an exon as described by Alberts, B. et al. at p. 373 of *Molecular Biology of the Cell* (1994), 3rd ed. Garland Publishing, N.Y. Splice Acceptors comprise a polypyrimidine tract followed by a nucleotide (N), followed by T or C and AG (3' intron portion), followed by at least G or A (5' exon portion) Examples are the murine En-2 splice acceptor and the splice acceptors from human β-globin and rabbit b-globulin.

The following examples are offered by way of illustration of the invention and not by way of limitation.

Example 1

Complementation trap vectors may be developed based on the alpha complementation of β-galactosidase.

Vectors

Figure 1:
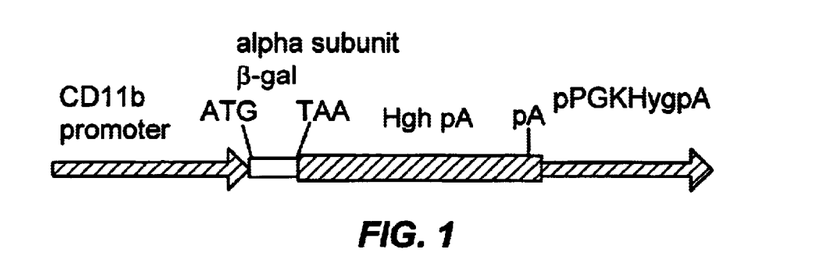
FIG. 1: is a schematic illustrating a DNA construct useful in this invention comprising the myeloid cell specific promoter CD11b controlling the sequence encoding a β-galactosidase alpha peptide terminated by the human growth hormone poly-adenylation signal. Downstream is a selection cassette, which in this case confers resistance to hygromycin driven by the phosphoglycerate kinase promoter.

FIG. 1 illustrates a CD11b alpha vector. The alpha subunit of beta-galactosidase is obtained by polymerase chain reaction (PCR) amplification using the following oligos from the pCMV β-galactosidase plasmid: oligo 1 corresponds to the polylinker sequence 5' of β-gal ($^{5'}$AACTGCAGT ACCCGCGGCCGC$^{3'}$ SEQ ID NO: 1) and the oligo 2 introduces stop codons at a position corresponding to amino acid 85 of the *E.coli* lacZ sequence: ($^{5'}$AACTGCAGTTAT TACTCAGGAAGATCGCACTCCAGC$^{3'}$ SEQ ID NO: 2). The PCR fragment is subcloned into pBluescript™. The alpha subunit is then subcloned into the Bam HI site of the CD11b expression cassette containing the CD11b promoter and the human growth hormone mini gene and polyadenylation signal described in; Dzienni, S., et al. (1995) *The CD11b Promoter Directs High-Level Expression of Resorter Genes in Macrophages in Transgenic Mice*. Blood 85:319–329. The CD11b alpha vector also contains a pPGK Hygro pA cassette allowing for selection with hygromycin. The alpha fragment was also subcloned into the CMV promoter expression cassettes (Clontech).

Figure 2:
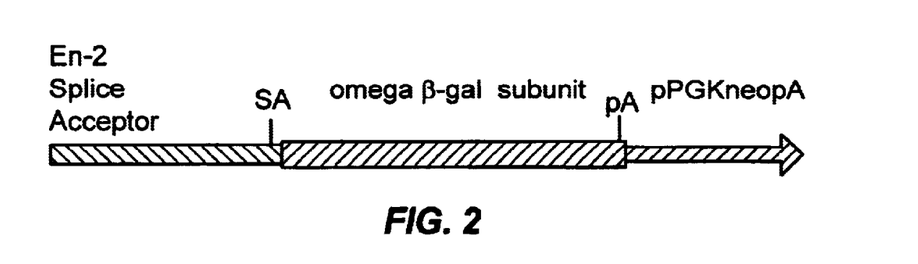
FIG. 2: is a schematic illustrating a DNA construct useful as a trap vector of this invention comprising the mouse En-2 splice acceptor upstream of the coding sequence of the β-galactosidase omega peptide and a selection cassette for neomycin resistance.

The omega trap vector illustrated in FIG. 2, is a derivative of pGT4.5 (Gossler et al., 1989 [supra]). The DNA fragment beginning at the unique BglII in the polylinker sequence between the En-2 splice acceptor sequence and the beginning of the β-gal sequence up to the unique ClaI site within the β-gal sequence from pFT4.5 is replaced by a PCR fragment amplified from pCMVbgal using the following oligos which delete the first 41 amino acids from the N-terminal sequence of β-galactosidase resulting in the β-galactosidase sequence to begin at amino acid 42 of the *E.coli* β-galactosidase sequence to the unique ClaI site in that sequence. Oligo 1 ($^{5'}$CGGGATCCCAAGATC TGGGC-CCGCACCGATCGCCCTTCC$^{3'}$ SEQ ID NO: 3); Oligo 2 ($^{5'}$CGGGATCCATCGATAATTTCACCGCCG$^{3'}$ SEQ ID NO: 4). PCR product is digested with BglII and ClaI and is directly inserted into the BglII-ClaI fragment of pGT4.5 vector. Three forms of this vector can be created; each resulting in a fusion in one of the three transcriptional reading frames.

Figure 3:
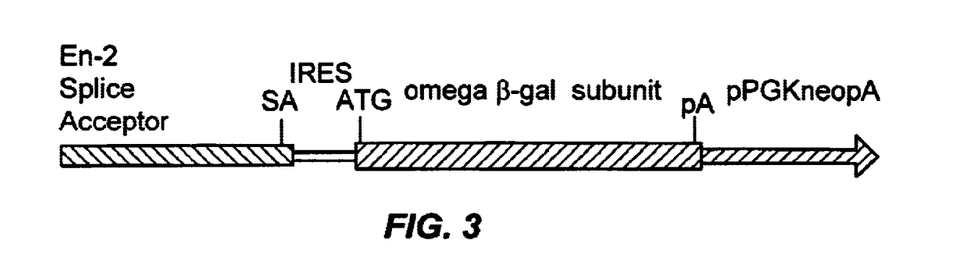
FIG. 3: is a schematic illustrating a trap vector of this invention in which a IRES sequence is positioned upstream of the β-gal omega sequence shown in FIG. 2.

FIG. 3 illustrates an omega trap vector with the IRES sequence from EMCV (Clontech) inserted between the En-2 splice acceptor and the omega subunit. In this case, translation of the omega subunit will be independent of the endogenous translation initiation codon and start at the ATG codon present in the IRES sequence. This IRES sequence has been shown to work in all tissues and does not have any tissue specificity for IRES function. Other IRES suitable for use in vector of this invention are known and are derived from various viral sources including: EMCV, poliovirus, picornavirus, Hepatitis C virus, HTLV-1, Friend murine leukemia virus, Moloney murine leukemia virus, Theiler's murine encephalomyelitis virus, apthovirus, Hepatitis A virus, ECHO virus, rhinovirus, enterovirus, cardiovirus, and pestivirus.

Figure 4:
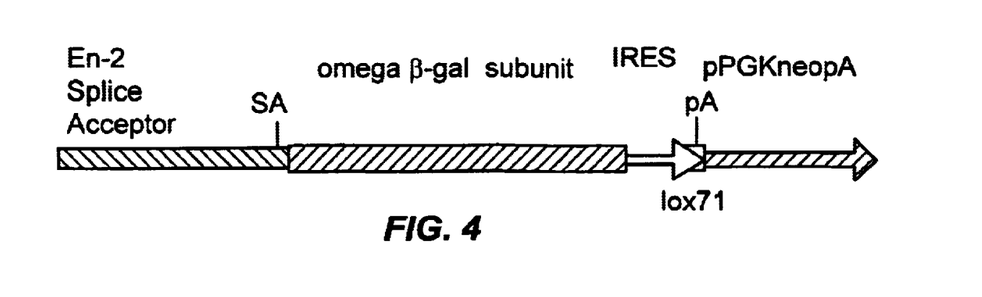
FIG. 4: is a schematic illustrating a trap vector of this invention in which a IRES sequence and a lox site are positioned downstream of the β-gal omega peptide coding sequence shown in FIG. 2.

FIG. 4 illustrates an omega trap vector with a IRES sequence followed by a lox7 site between the omega gene and the poly adenylation signal. This example may also be carried out using CD11b to drive the omega subunit and a trap vector comprising the alpha subunit.

The N terminal sequence of Neo to the unique Ba1 I site in Neo is fused to the omega fragment of β-galactosidase starting at the unique FsoI site in β-galactosidase in the trap vectors illustrated in FIGS. 2–4. The fusion protein is driven by the Herpes thymidine kinase promoter and polyoma enhancers and has the SV40 polyA signal.

β-gal Complementation

To test whether the omega fragment as a fusion protein is capable of complementation with the alpha fragment, vectors were constructed to express a portion of the Neo gene fused to the β-gal omega peptide described above under control of the human cytomegalovirus immediate—early gene (CMV) promoter. As a fusion with the neo gene product, the omega peptide was found to be capable of complementing with the alpha fragment in 293 kidney cell line. Transient transfection by Superfection™ (Qiagen) of 293 cells with alpha fragment driven by CMV promoter alone or the omega fragment alone showed background levels of enzyme activity whereas the combination of the aloha and omega subunits resulted in detectable enzyme activity by the luminescent β-galactosidase Genetic Reporter System II™ from Clontech.

The alpha subunit prepared as described above was excised from pBluescript™ using NotI and sublconed into the NotI site of the pIRES1hyg expression vector (Clontech) resulting in a bicistronic expression vector, pCMValpha, containing the human cytomegalovirus (CMV) major immediate, early promoter/enhancer driving the expression of the alpha subunit followed by an IRES Hygromicin (which predisposes virtually every hygromycin resistant transfected cell to express the alpha gene). The mCMValpha vector and the omega trap vector containing the IRES sequence, pGT omega IRES (as described above) were used to demontrate β-gal complementation in ES cells. $R_1$ ES cells (Nagy, A. [supra]) were electroporated with the HindIII linearized pCMValpha plasmid DNA. Clones were then selected in the presence of 100 μg/ml Hygromycin. A polyclonal hygromycin resistant pool was expanded and then electroporated with HindIII linearzied pGT omega IRES DNA. Clones were selected with 180 μg/ml G418. Individual colonies were picked and transferred to 96 well plates. Individual clones were then analyzed for β-gal activity using the β-gal genetic reporter II Kit from Clontech. One in 50' clones showed complementation activity in ES cells.

ES Cell Culture, Selection and Gene Insertion

Murine R1 ES cells from A. Nagy [Proc. Nat. Acad. Sci. U.S.A. (1993) 90, 8424–8428] may be grown on Primary Embryonic Fibroblast feeder layers or on gelatinized dishes in the presence of 1000 U/ml murine leukemia inhibitory factor (LIF), ESGRO™ (GIBCO BRL). Selection conditions are: 150 μg/ml G418, 1.0 μg/ml puromycin, 110 μg/ml Hygromycin B. $2 \times 10^7$ R1 cells may be electroporated with 100 μg linearized DNA in 0.8 ml PBS at 500 μF and 240V with a BioRad Gene Pulser™ at room temperature.

The ES cells may be electroported with CD11b promoter driving the alpha subunit and selected with hygromycin to obtain stable clones. Clones would then be selected and characterized by the expression pattern of the alpha subunit. Clones are isolated which express the alpha subunit in myeloid cells. The omega trap vector would then be electroported into CD11b alpha ES cells. Cells would then be plated into 96 well plates to obtain approximately 10 Neo resistant clones per well with 150 μg/ml G418. Clones should be replica plated in duplicate. One set is frozen and one set allowed to differentiate and assayed for β-gal activity. Positive wells would be identified and individual cells subcloned and assay is repeated on individual clones. The following protocol may be used:

Picking of Individual ES Cell Colonies:
1) plate out cells at low dilution;
2) grow for 9–12 days allowing individual cells to grow into individual colonies;
3) pick individual colonies in 5 to 10 μl volume using a P20 Gilson Pipetman™;
4) transfer colonies into 50 μl Trypsin/EDTA Gibco/BFL) in a 96 well round bottom plate;
5) incubate for 5 min at RT;
6) add 50 μl fresh serum containing ES cell media
7) disrupt colonies to single cell suspension by pipetting up and down; and
8) replate cells on gelatinized tissue culture plates and add fresh media as necessary.

Freezing ES cells in 96-well plates:
1) aspirate off media;
2) replace with 30 μl freezing media per well. (Freezing media contains: 50% serum, 10% DMSO, 40% DMEM, 1000U/ml LIF); and
3) transfer plate into −70° C. freezer in a styrofoam box.

Thawing ES Cells in 96 Well Plates:
1) add 100 μl prewarmed ES cell media per well;
2) incubate cells at 37° C. 5% $CO_2$ for 6–8 hours; and
3) replace with fresh media.

Expression patterns of the alpha subunit may be characterized by in situ hybridization or immunohistochemistry using a monoclonal or anti-peptide antibody raised against the alpha peptide; immunofluorescence dual labelling with anti-alpha peptide and anti-MAC-1 (CD11b); or, by transfecting cells with CMV promoter driving the expression of the omega fragment and detecting β-gal activity.

In an alternative procedure, the ES cells would be electroported with CD11b promoter driving expression of alpha subunit and selected with hygromycin to obtain stable clones. Several clones would be identified and the expression pattern of the alpha subunit characterized in order to isolate clones which express the alpha subunit in myeloid cells. The omega trap vector containing IRES and lox71would be electroplated into the CD11b alpha ES cell. The cells would then be plated in a 96 well plate to obtain approximately 10 Neo resistant clones per well. Clones would then be selected with 150 μg/ml G418 and replica plated in duplicate. One set would be frozen and one set allowed to differentiate and assayed for β-gal activity. Positive wells would be identified and individual cells subcloned with the assay being repeated on individual clones. Heterologous DNA would then be introduced into trapped events by co-electroporation of a transgene as a circular plasmid containing a single mutant lox (lox66) site with CRE expression cassette for transient expression of CRE. Stable integration of the transgene would be determined by selection for a resistance gene found on transgene vector (eg. Araki et al., 1997 *Targeted Integration of DNA Using Mutant lox Sites in Embryonic Stem Cells*. Nucleic Acids Research 25, 868–872).

Preferential differentiation of ES cells to obtain macrophage cells may be accomplished by known procedures, including those described by: Lieschke, G. J. and Dunn, A. R. *Development of Functional Macrophages from Embryonal Stem Cells In Vitro*. (1995) Experimental Hematology 23(4):328–334. Alternatively, chimeric embryos and resulting chimeric mice may be obtained by injection of the ES cells into blastocysts, eg. C57BL/6 blastocysts.

5' RACE Cloning

5' Rapid PCR amplification of cDNA ends (RACE) may be carried out as described by Skarnes, et al. at (1992) Genes and Development 6, 903–918, to clone a portion of the endogenous gene flanking the omega component insertion. This provides fragments for sequencing and to probe for genes. The source of reagents may be the 5' RACE kit commercially available from Gibco-BRL. An additional round of nested PCR may be performed. Macrophage cells may be enriched by Fluorescent Activated Cell Sorting (FACS) or immuno-magnetic bead purification prior to RNA isolation. PCR products may be subcloned into pBluescript™. In order to confirm the sequences of the trapped exons, 5–10 bacterial colonies should be picked from each line and the isolated plasmid DNAs sequenced by standard double strand sequencing protocols. High throughput solid phase sequencing of 5' RACE PCR product is describe in Townley, D. J. et al. (1997) *Rapid Sequence Analysis of Gene Trap Integrations to Generate a Resource of Insertional Mutations in Mice*, Genome Research 7:293–298.

Choice of Complementation Systems:

The optimal choice of a complementation system will depend on the following criteria: the given target tissue or cell type from which gene trap events are to be identified, the level of expression of endogenous activity of the kind exhibited by the complementation components in the given tissue or cell type, and the ability of the cells to differentiate in vitro and then dependence on other cell types for growth.

If one targets macrophage cells to identify macrophage specific genes using β-gal complementation, consideration should be given to the fact that macrophage cells display a background level of endogenous β-gal activity. Therefore, the alpha complementation of β-gal may not be the ideal complementation system of choice for macrophage cells since the detection of activity of complemented β-gal may be compromised. The activity of the complemented β-gal can be approximately 25–200 fold weaker than that of wild-type lacZ, as demonstrated in 293 cells and in NIH3T3 cells (Mohler and Blau 1996 [supra]) coexpressing alpha and omega subunits of β-gal.

Because of potential for low activity of complemented β-gal, the most a sensitive detection systems (such as assays based on fluorescence use of a luminometer and reagents such as Gatacton-plus™, or those in the Galacto-star™ kit) should be used when employing alpha-complementation of β-gal. Steps should be taken using known methods to reduce background β-gal activity such as adjustment of temperature or pH. For tissues which do express endogenous β-gal, it may be advisable to chose an alternate reporter system.

Use of Alpha Complementation of β-gal in Identification of Neural Specific Genes Alpha complementation of β-gal may be particularly suited for identification of neural specific genes since ES-derived neuronal cells do not display endogenous β-gal activity in vitro. This enzyme complementation system may make use of the rat 1.8 kb neuron-specific enolase promoter (NSE) to identify gene trap events in neuronal cell restricted genes in the construction of vectors as described in FIG. 1 in which the CD11b promoter is replaced with the NSE promoter. The in vitro expression profile of the NSE promoter in differentiated ES cells has been previously characterized (Alouani S. et al. (1993). Transcriptional Activity of the Neuron-Specific Enolase (NSE) Promoter in Murine Embryonic Stem (ES) Cells and Preimplantation Embryos. European Journal of Cell Biology. 62(2):324–32; 1993.

Vectors

A vector with NSE driving the alpha subunit of β-gal was produced by introduction of stop codons by ligation of overlapping oligomers into the ClaI site of: pNSEβgal mode according to Alouani, et al. (1993) [supra]. NSE $\Delta\mu$ as a second vector for neuronal expression of the donor alpha peptide fragment was generated by deleting 553 codons of the lacZ gene in pNSE-βgal between two in frame PvuI sites. The omega trap vector with IRES as described in FIG. 3 was also used.

Linearized NSE alpha and NSE $\Delta\mu$ DNA were transfected into RES cells by co-electroporation with linearized PGKHyg DNA. Clones were selected with 110 $\mu$g/ml Hygromycin and picked as describe below. Individual clones were characterized for alpha subunit expression by in situ hybridization of in vitro derived neuronal cells using the differentiation protocol described below. Clones expressing alpha donor genes were subsequently electroporated with the omega IRES gene trap vector and colonies were selected with 150 $\mu$g/ml G418. Individual clones were picked and replica transferred to 96 well plated in triplicate. One plate was frozen for storage, a second plate to be assayed for β-gal activity and the third plate was in vitro differentiated as describe below into neuronal lineage to be assayed for β-gal activity.

In Vitro Differentiation of ES Cells into Neuronal Lineage

1. Split ES cells two days prior.
2. Change media on day prior.
3. Start differentiation. Trypsinize to single cells. Wash one with PBS.
4. Resuspend in 15–20 ml media
   7.5% FBS
   7.5% NBCS (lot tested)
   DMEM (no LIF)
   $10^{-4}$ M bME
5. Plate $1.5 \times 10^6$ cells per 10 cm bacterial grade petri dish.
6. Incubate at 37° C. 6% $CO_2$ 7 days to form embryoid bodies (EB).
7. Collect EB in 50 ml conical tube. Allow bodies to settle to bottom of tube and remove supernatant.
8. Wash EB in PBS (30 ml).
9. Aspirate of f PBS leaving 1 ml PBS. Add 3 ml Trypsin. Incubate for 5 minutes at 37° C. taking care not to over trypsinize by monitoring trypsinization of EB under a microscope by transferring some EB to a 6 cm dish.
10. After trypsinization, pipette up and down to break up EB to single cell suspension. Trypsinize for an additional 1–2 minutes if there are still large clumps.
12. Count healthy cells.
13. Plate out densities of $2 \times 10^5$ and $4 \times 10^5$ on 3.5 cm dishes containing a mouse laminin (Becton Dickinson) coated coverslip. Final volume per dish is 2 ml. Avoid large clumps of cells by allowing them to settle out. Small clumps of 4–5 cells are desirable. Change media at 4–5 days. Analyze neuronal cells for β-gal activity after 7 days by staining with Xgal™ or by more sensitive techniques as described herein.

EXAMPLE 2

Transcriptional Activation (Two Hybrid System)

The two hybrid system is based on the fact that many eucaryotic transcriptional activators are comprised of two physically and functionally separable domains, a DNA-binding domain (DNA-BP) and an activation domain (AD). The two domains are normally part of the same protein. However, the two domains can be separated and expressed as distinct proteins. Two additional proteins (X and Y) are expressed as fusions to the DNA-BP and AD peptides. If X and Y interact, the AD is co-localized to the DNA-BP bound to the promoter, resulting in the transcription of the reporter gene.

The following is an example of the two hybrid transcriptional activation gene trap system. This system is composed of two fusion proteins, one component of which is expressed by a tissue- or cell- specific promoter and the second is found in a gene trap vector:

1) a fusion of protein X with the GAL4 DNA-BP;
2) a fusion of protein Y with the VP16 activation;

where protein X and Y interact (for example: the SV40 large T antigen which associates with the p53 protein). A third vector provides the GAL4 DNA binding site, the minimal promoter of the adenovirus E1b, and the lacZ reporter gene.

ES cells are first "seeded" with the third vector and a tissue-restricted promoter driving one component, for example: the CD11b promoter driving the expression of the GAL4 DNA-BP fused to p53 peptide sequence. The vector may also contain a selectable marker such as PGK neo. The cells are then transfected with the second component found in a gene trap vector system. The gene trap vector may contain a gene encoding a fusion protein comprising the VP16 activation domain fused to the SV40 large T antigen preceded by a splice acceptor sequence and a IRES. The vector may also contain a selectable marker such as PGK-hygro. The ES cells are replica plated and some cells are allowed to differentiate and are then screened for β-gal activity.

Another example of this embodiment would be to use the following fusion proteins:

1) the GAL4 DNA binding domain fused to the Fos leucine zipper domain (DFosLZ), and
2) the VP16 activation domain fused to the Jun leucine zipper (AJunLZ); or
1) the GAL4 DNA binding domain fused to the Jun leucine zipper domain (DJunLZ), and
2) the VP16 activation domain fused to the Fos leucine zipper (AFosLZ).

The construction of these vectors have been previously described in Dang et al., (1991) Molecular and Cellular Biology, 11:954–962, and components to create the vectors of this system (except leucine zipper components) may be obtained from Clontech-Mammalian Matchmaker™ two hybrid assay kit.

An example of a reporter system whose expression is dependent on the presence of two interacting fusion proteins is the G5E1bCAT vector which contains 5 copies of the 17 mer GAL4 DNA binding site 5' of the minimal promoter of the Adenovirus E1b driving the expression of the CAT reporter gene. The CAT reporter gene may also be replaced by the β-gal reporter gene or any other reporter gene. In order to adapt this to the complementation gene trap system, one component (for example DFosLZ) is driven by a tissue restricted promoter such as the CD11b promoter. The DFosLZ gene can be subcloned into a CD11b expression cassette (eg. as described in Dziennis, S. et al. (1995), Blood 85:319–329). The second component will be contained in a gene trap vector. The trap vector will be a variation of the IRES containing gene trap system described by Chowdhury et al., [supra] where the βgeo gene is replaced with the AJunLZ gene.

EXAMPLE 3

Transcriptional Activation (Genetic Recombination Dependent)

This system makes use of a vector containing a stuffer DNA fragment flanked by lox sites preceding a reporter gene similar to that described by Lasko, et al., (1992): *Targeted Oncogene Activation by Site-Specific Recombination in Transgenic Mice*; Proc. Natl. Acad. Sci. USA 89:6232–6236. The expression of the reporter gene is dependent on the removal of the stuffer DNA sequence mediated by the Cre recombinase enzyme through site directed recombination of lox sites found flanking the stuffer DNA. The gene trap vector contains the Cre gene preceded by a splice acceptor sequence and an IRES. The gene trap vector may also contain a selectable marker.

EXAMPLE 4

Selection/Screening System

In this embodiment, a selectable marker is driven by a tissue restricted promoter. For example, the myeloid specific promoter CD11b may drive the expression of the puromycin resistance gene (puromycin n-acetyl transferase, pac). Such a vector may also contain PGK-hygro for ES cell selection. Cells would be transfected with a gene trap vector such as pGT4.5 which contains the lacZ reporter, and then allowed to differentiate and subsequently placed under selection with puromycin. Only myeloid specific cells survive the selection protocol. Those cells are then assayed for the expression of the reporter gene.

One factor that may influence the choice of embodiment or this invention is the ability of a chosen cell (eg. ES cells), to differentiate into a given cell type in vitro and the requirements of the specialized cells in order to grow and survive in the absence of other cell types (such secondary stromal cells or feeder cells). If a specialized tissue or cell type is dependent on a second cell type for growth and survival, use of this section/screening embodiment may not be the ideal embodiment of this invention to use.

Since macrophage display endogenous β-gal activity which tends to mask complemented β-gal activity, and because macrophage cells can differentiate from hemopoietic stem cells in the absence of stromal cell interaction (when cytokines are added to suspension culture), the selection/screening system was carried out in a modification of the methods described in Example 1. This Example relies on expression of the entire lacZ gene and not alpha complementation of β-gal fragments. In order to differentiate between endogenous β-gal activity and the lacZ activity, a staining protocol at pH 8.5 that selectively detected lacZ activity and suppressed endogenous β-gal activity was employed. Also, use of the Galacto-star™ kit was shown co preferentially detect lacZ activity over endogenous mammalian β-gal.

Vectors

A CD11b PURO vector was constructed as follows: a 660 bp Sal I/HindIII fragment encoding the Puromycin acetyl transferase gene derived from pMXPURO construct was blunt ligated into the BamHI cloning site of the CD11b expression cassette containing the CD11b promoter and the human growth hormone minigene and polyadenylation signal, as described in Dzienni, S., et. al. (1995) [supra]. A pGT4.5 gene trap vector containing the full length lacZ gene as described in Gossler, A. et al. (1989) [supra] was a gift from the laboratory of Dr. J. Rossant (Toronto, Ontario). A vector containing EMCV IRES flanked by BgIII sites was generated by digesting the pGT1.8IRESβgeo vector which was a gift of Dr. Austin Smith (described in Mountford, P. et al. (1994). Proc. Natl. Acad. Sci. U.S.A 91:4303–4307) with NcoI and ligating with self-overlapping oligomer 5' CATGGAGATCTC3' (SEQ. ID NO:5). The IRES sequence was then excised by digestion with pGT4.5 gene trap vector. A pGT4 IRES trap vector was constructed by ligating the BgII IRES fragment into the unique BgIII site in the pGT4.5 vector.

ES Cell Culture $R_1$ cells (Nagy et al. [supra]) were maintained in DMEM medium containing 15% FBS, 1000 U/ml LIF, $10^{-4}$ M BMe, 2 mM L-Glutamine, 1 mM Na Pyruvate, 50 IU Penicillin/50 μg/ml Streptomycin, 0.1 mM non-essential amino acids (NEAA). To obtain stable lines between $5 \times 10^7$ and $1 \times 10^8$ cells were co-electroporated with 20 μg CD11bPURO and 1 μg PGK Hyg linearized plasmid DNA in a volume of 0.8 ml PBS using a BioRad Gene Pulser™ set at (240V 500 μF). $5 \times 10^6$ cells were plated on gelatinized 10 cm tissue culture dishes and colonies were selected in 110 μg/ml Hygromycin. Gelatinization of tissue culture dishes was accomplished by coating the surface with o.1% gelatin (SIGMA) for at least 10 minutes before aspiration of gelatin solution and allowing to air dry.

Selection of Clones that Express Puromycin in a Tissue Restricted Manner as Defined by the Chosen Promoter Embryonic stem cells were co-electroporated with 20 μg CD11b PURO vector linearized with HindIII and with lug PGKHyg linearized with HindIII plasmid DNA. Cells were cultured in ES cell medium containing LIF on gelatinized tissue culture dishes in the presence of 110 μg/ml Hygromycin. After 9 days of culture, individual clones were picked and replica transferred into duplicate gelatinized 96-well tissue culture dishes to obtain one hygromycin resistant clone per well. Cells on one dish were stored by freezing. Cells on the second dish were caused to differentiate in vitro.

In Vitro Differentiation of CD11bPURO ES Cells into Hemopoietic Lineage

Iscove's differentiation medium was prepared as follows:
Iscove's MDM medium
15% fetal bovine serum #603—special batch tested serum for hemopoietic cell differentiation
2 mM glutamine
450 uM monothioglycerol, MTG
40 ng/ml steel factor
10% 10× concentrated 3T3 conditioned medium
4% 10× concentrated Wehi 3 conditioned medium In vitro differentiation of CD11bpuro ES cells begin with the primary cultures, which after 8 days result in the formation of several large embryoid bodies. These embryoid bodies were disrupted to obtain a single cell suspension which was subsequently cultured in the presence of puromycin for eight days. This secondary culture leads to the selection of hemopoietic cells, primarily macrophages.

Primary Cultures

First, clones that were grown to 70% confluency on tissue culture treated 96 well plates were trypsinized by adding 20 μl of Trypsin-EDTA to each well and incubated for 5 minutes at 37° C. Once the cells became detached, 60 μl of Iscove's medium as described above with 5% serum was added to each well. Following vigourous mixing to break up clumps of cells and to obtain a single cell suspension, 20 μl volumes from each clone were added to each of three low binding well Costar™ plates that already contained 180 μl per well of differentiation medium. These plates were then incubated by 37° C. and 6% $CO_2$ for eight days changing media when necessary. The remaining 20 μl aliquots were transferred to a DMEM ES growth media-containing LIF in a 24 well plate and incubated to reach confluency and frozen.

Secondary Cultures

Following eight days of incubation of the primary embryoid body cultures, the media was carefully removed using a multichannel pipettor. The embryoid bodies were washed three times with PBS. Subsequently, 100 μl of Trypsin-EDTA was added to each well and the plates were incubated for 10 minutes at 37° C. The embryoid bodies were then disrupted by mixing 10 to 20 times with a multichannel pipettor and the single cell suspension was transferred to a round-bottom 96 well plate. These plates were centrifuges for 5 minutes at 1200 rpm and the cell pellets were resuspended in differentiation medium containing puromycin at 0.2 μg/ml and transferred to Costar™, low binding 96 well plates. The plates were then incubated for a further eight days at 37° C. and 6% $CO_2$, changing media when necessary. Cytospin analysis and staining of cells with May-Grunwald/Giemsa revealed that the majority of cells derived from the above culture conditions had a macrophage morphology. A CD11bPURO transfected ES cell clone (1D) was chosen due to its reproducibility in vitro to differentiate into a macrophage lineage upon culture with the above cytokine/growth factor cocktail and the presence of puromycin.

Electroporation of Gene Trap Vector

10 μg of ScaI linearized pGT4IRES or pGT4.5 DNA was electroporated into the 1D ES cells, After 9 days of culture in the presence of 180 μg/ml G418. 265 clones were picked and replica transferred into triplicate 96 well plates. One plate of cells was stored by freezing, another plate was stained with Xgal™ to analyze the expression of β-gal in the ES state and a third plate was differentiated in vitro into the hemopoietic lineage (as described above) and then stained with Xgal™. One in 38 clones were positive in GT4IRES trapped ES clones, where one in 96 clones were positive using the GT4.5 gene trap vector. One in 200 clones were positive in macrophage cells using the GT4IRES vector. Staining for β-gal activity in macrophage was done at pH8.5 in order to suppress endogenous β-gal activity and selectively detect the gene trap vector derived lacZ activity. No background activity was detected at pH 8.5, thus the presence of stain was a positive event.

EXAMPLE 5

Co-expression of Two Reporter Genes

An example of this embodiment is where ES cells are first seeded with one reporter (such as the human CD8 cell surface protein) driven by a myeloid specific promoter, such as CD11b. The vector may also contain a selectable marker such as PGK hygro for ES cell clone selection. The cells are then transfected with a gene trap vector comprising, for example, the green fluorescent protein preceded by a splice acceptor sequence and followed by an IRES sequence. The gene trap vector may also contain a selectable marker such as PGK neo. Individual clones are replica plated and some cells are allowed to undergo differentiation and are subsequently screened for dual expression of the reporter genes by immunofluorescence and FACS analysis. The cells are stained with a monoclonal antibody directed against the human CD8 cell surface protein that is conjugated to phycoerythrin. Cells are then subsequently analysed for red and green fluorescence by FACS.

EXAMPLE 6

Luciferase—GFP Pathway

A pathway system that may be utilized is a luciferase and green fluorescent protein (GFP) system derived from bioluminescent coelenterates such as the jellyfish Aeauorea victoria or the sea pansy *Renilla reniformis*. The GFP serves as an energy-transfer acceptor, receiving energy from a Ca2+-activated photoprotein or a luciferase-oxyluciferin complex in A. victoria and *R. renifirmis*, respectively. Aequorin is a 21 kDa apoprotein which is complexed with molecular oxygen and coelenterazine. When aequorin is activated by Ca2+, it catalyzes the oxidation of the coelenterazine to coelenteramide, which is in an activated state. Ceolenteramide returns to its ground state, emitting blue light at 470 nm. Energy transfer to GFP occurs from the excited state of coelenteramide complex with aequorin. GFP absorbs 470 nm light energy from activated aequorin and emits green light at 510 nm.

The following procedure demonstrates this pathway system in human embryonal kidney cells. pQB125 (Quantum Biotechnologies Inc.) is a vector containing the red shifted mutant coding sequences of green fluorescent protein (GFP) driven by the CMV promoter. A pCMV-Aequorin vector was prepared according to Brini, et al. (1995) J. Biol. Chem. 270:9896–9903. Transient transfection by "superfection (QIAGEN) was performed according to the manufacturer's instructions. Human 293 embryonal kidney cells were transfected with pQB125 alone, pCMV-Aequorin vector alone or with pQB125 and pCMV-Aequorin. After 24–48 hours post transfection, cells were incubated with a solution containing PBS and 125 μm Coelenterazine (Molecular Probes, Oregon) for 30 minutes. Cells were then washed once with PBS and lysed with 0.1% Triton X-100™ and 50 mM CaCl$_2$ solution. Luminescence was measured in a MLX™ Microtitre plate luminometer (DYNEX). Samples were performed in duplicate and read with and without a longwave bandpass filter (500 nm cutoff; Chromatech) added to the luminometer detector to block out transmission of wavelengths below 500 nm. The results are set out below.

| Plasmids Transfected | Relative Light Units (RLU) Without Filter (0–600 nm) | Relative Light Units With Filter | Percent Transmission |
|---|---|---|---|
| pCMVAequorin | 114 632 | 18 296 | 16% |
| pQB125 | 1 131 | 215 | 19% |
| PCMVAequorin + pQB125 | 121 937 | 59 266 | 49% |

This example may be adapted for use in this invention by preparation of DNA constructs similar to those shown in the Figures. A trap vector is prepared by placing either the Aequorin or the GFP coding sequence downstream of a splice acceptor with an optional IRES upstream of the coding sequence. A vector containing the desired promoter having restricted expression is prepared in which the promoter drives either the Aequorin or the GFP coding sequences.

All publications and patents cited in this specification are incorporated herein by reference. Although the foregoing invention has been described in some detail by way of illustration and example for purposes of clarity of understanding, it will be readily apparent to those of skill in the art in light of the prior art and the teachings of this specification that various changes and modification may be made to the invention described without rill departing from the spirit or scope of the appended claims.

We claim:

1. A method of screening for the integration of a DNA construct into a target gene having expression in the same cell or tissue type in which a promoter having restricted expression in a mouse is active, said method comprising:
   (i) transforming a mouse ES cell with a first DNA construct encoding a first indicator component under the control of said promoter;
   (ii) transforming the cell of (i) or a descendent of the cell by operably integrating into the cell's genome, a second DNA construct comprising DNA encoding a second indicator component not operably linked to a transcription control element;
   (iii) producing tissue or specialized cells from the cell of (ii); and
   (iv) monitoring the tissue or specialized cells of (iii) for a detectable indicator resulting from both the first and second indicator components indicative of integration of the second DNA construct into said target gene.

2. The method of claim 1 wherein the first and second indicator components are inactive fragments or subunits of an enzyme which, when combined, provide an active enzyme detectable by its activity.

3. The method of claim 1 wherein the first and second indicator components are independently detectable or selectable, and the detectable indicator is the presence of both indicator components in a cell.

4. The method of claim 1 wherein the first and second indicator components react in a sequence of reactions which result in a detectable indicator.

5. The method of claim 1 which additionally comprises isolating DNA endogenous to the mouse ES cell or descendent thereof which flanks the second DNA construct integrated into said target gene.

6. A DNA construct comprising, in a 5' to 3' direction, a splice acceptor, a sequence encoding an inactive subunit or fragment of an enzyme and, an IRES wherein said sequence encoding the enzyme subunit or fragment is not operably linked to a transcription control element, and wherein said subunit or fragment is active when combined with a further subunit.

7. A composition comprising a combination of:
   (i) a DNA construct for integration into the genome of an eukaryotic cell comprising a sequence encoding a first indicator component under the control of a promoter having restricted expression; and
   (ii) a DNA construct for integration into the genome of a eukaryotic cell, comprising in the 5' to 3' direction, a splice acceptor, a sequence encoding a second indicator component not operably linked to a transcription control element, and an optional IRES, wherein expression of both the first and second indicator components in said cell is detectable, and wherein if said first indicator component is an antibiotic resistance marker, said second indicator component is not an antibiotic resistance marker.

8. A mouse ES cell or descendent thereof, transformed by the composition of claim 7, wherein said promoter has restricted expression in a mouse.

9. A DNA construct comprising, in a 5' to 3' direction, a splice acceptor and a sequence encoding an inactive alpha or omega fragment of β-galactosidase, wherein said sequence encoding the inactive alpha or omega fragment is not operably linked to a transcription control element and said fragment is active when combined with another fragment of β-galactosidase.

10. A method of screening for the integration of a DNA construct into a target gene having expression in the same cell or tissue type in which a promoter having restricted expression in a mouse is active said method comprising:
  (i) transforming a mouse ES cell with a first DNA construct encoding a first indicator component linked to said promoter, wherein DNA encoding the first indicator component is separated from said promoter by a sequence of DNA which prevents transcriptional control by said promoter over the DNA encoding the first indicator component;
  (ii) transforming the cell of (i) or a descendent of the cell by operably integrating into the cell's genome, a second DNA construct comprising DNA encoding a second indicator component not operably linked to a transcription control element;
  (iii) producing tissue or specialized cells of (ii); and
  (iv) monitoring the tissue or specialized cells of (iii) for a detectable indicator resulting from both the first and second indicator components indicative of integration of the second DNA construct into said target gene, wherein in the second DNA construct, the second indicator component is a recombinase capable of removing the sequence of DNA preventing transcriptional control in the first DNA construct; and,
  wherein said monitoring is for cells in which the first indicator component is expressed under the transcriptional control of the promoter having restricted expression.

11. The method of claim 10 wherein the DNA preventing transcriptional control is flanked by lox sites and the recombinase is Cre.

12. A method of producing mouse tissue or specialized cells comprising a detectable indicator associated with a target gene having expression in the same cell or tissue type in which a promoter having restricted expression in a mouse is active, which comprises:
  (i) transforming a mouse ES cell with a first DNA construct encoding a first indicator component under the control of said promoter;
  (ii) transforming the cell of (i) or a descendent of the cell by integrating into the cell's genome, a second DNA construct comprising DNA encoding a second indicator component not operably linked to a transcription control element;
  (iii) producing tissue or specialized cells from the cell of (ii); and
  (iv) selecting tissue or specialized cells of (iii) by the presence of a detectable indicator resulting from both the first and second indicator components.

13. A method of producing a mouse comprising a detectable indicator associated with a target gene having expression in the same cell or tissue type in which a promoter having restricted expression in a mouse is active, which comprises:
  (i) transforming a mouse ES cell by integrating into the cell's genome, a first DNA construct encoding a first indicator component under the control of said promoter;
  (ii) transforming the cell of (i) or a descendent of the cell by integrating into the cell's genome, a second DNA construct comprising DNA encoding a second indicator component not operably linked to a transcription control element;
  (iii) selecting transformed cells of (ii);
  (iv) introducing selected cells of (iii) into a mouse host embryo;
  (v) implanting the host embryo of (iv) into a pseudopregnant mouse;
  (vi) maintaining the mouse of (v) while offspring develops to term from the host embryo; and
  (vii) selecting offspring of (vi) by the presence of a detectable indicator resulting from both the first and second indicator components in tissue or specialized cells of the offspring.

* * * * *